(12) United States Patent
Mattaboni et al.

(10) Patent No.: US 7,940,008 B2
(45) Date of Patent: May 10, 2011

(54) INDUCTIVELY-COUPLED RF POWER SOURCE

(75) Inventors: Paul J. Mattaboni, Surprise, AZ (US); Robert Mellor, Middlewich (GB); Roger Fletcher, Wirswall (GB)

(73) Assignee: Thermo Fisher Scientific, Inc., Waltham, MA (US)

( * ) Notice: Subject to any disclaimer, the term of this patent is extended or adjusted under 35 U.S.C. 154(b) by 140 days.

(21) Appl. No.: 12/265,870

(22) Filed: Nov. 6, 2008

(65) Prior Publication Data
US 2009/0058304 A1    Mar. 5, 2009

Related U.S. Application Data

(63) Continuation of application No. 11/285,530, filed on Nov. 21, 2005, now Pat. No. 7,459,899.

(51) Int. Cl.
*H05B 31/26* (2006.01)
*G01R 23/12* (2006.01)

(52) U.S. Cl. .................. 315/111.21; 324/76.53; 324/622

(58) Field of Classification Search .............. 324/76.53, 324/76.58, 600, 622, 633, 771; 315/111.21, 315/111.01, 111.71
See application file for complete search history.

(56) References Cited

U.S. PATENT DOCUMENTS

| | | | |
|---|---|---|---|
| 5,844,369 A * | 12/1998 | Yoshizako et al. | 315/111.21 |
| 6,351,693 B1 * | 2/2002 | Monie et al. | 700/299 |
| 6,917,204 B2 * | 7/2005 | Mitrovic et al. | 324/464 |
| 7,459,899 B2 * | 12/2008 | Mattaboni et al. | 324/76.53 |
| 7,602,127 B2 * | 10/2009 | Coumou | 315/111.21 |

* cited by examiner

*Primary Examiner* — Jacob Y Choi
*Assistant Examiner* — Jimmy T Vu
(74) *Attorney, Agent, or Firm* — Charles B. Katz (57) ABSTRACT

A system and method are disclosed for implementing a power source including a power amplifier that generates a radio-frequency power signal with an adjustable operating frequency. The power amplifier also generates a reference phase signal that is derived from the radio-frequency power signal. An impedance match provides the radio-frequency power signal to a plasma coil that has a variable resonance condition. A phase probe is positioned adjacent to the plasma coil to generate a coil phase signal corresponding to the adjustable operating frequency. A phase-locked loop then generates an RF drive signal that is based upon a phase relationship between the reference phase signal and the coil phase signal. The phase-locked loop provides the RF drive signal to the power amplifier to control the adjustable operating frequency, so that the adjustable operating frequency then tracks the variable resonance condition.

21 Claims, 9 Drawing Sheets

INDUCTIVELY-COUPLED RF POWER SOURCE

CROSS-REFERENCE TO RELATED APPLICATIONS

This application is a continuation of and claims the priority benefit under 35 U.S.C. §120 of U.S. patent application Ser. No. 11/285,530 entitled "Inductively Coupled RF Power Source," filed Nov. 21, 2005 now U.S. Pat. No. 7,459,899, the entire disclosure of which is incorporated herein by reference.

FIELD OF THE INVENTION

The disclosed embodiments of the present invention relate generally to techniques for implementing a power source, and relate more particularly to a system and method for implementing an inductively-coupled plasma radio-frequency (RF) power source.

BACKGROUND OF THE INVENTION

Implementing effective methods for implementing analytical instrumentation is a significant consideration for designers and manufacturers of contemporary electronic analytical devices. However, effectively performing analysis procedures with electronic devices may create substantial challenges for system designers. For example, enhanced demands for increased device functionality and performance may require more system functionality and require additional hardware resources. An increase in functionality or hardware requirements may also result in a corresponding detrimental economic impact due to increased production costs and operational inefficiencies.

Furthermore, enhanced system capability to perform various advanced operations may provide additional benefits to a system user, but may also place increased demands on the control and management of various device components. For example, an enhanced electronic system that analyzes certain organic substances may benefit from an efficient implementation because of the complexity and precision of the analysis involved.

Due to growing demands on system resources and increasing complexity of analysis requirements, it is apparent that developing new techniques for implementing analytical instrumentation is a matter of concern for related electronic technologies. Therefore, for all the foregoing reasons, developing effective techniques for implementing analytical instrumentation remains a significant consideration for designers, manufacturers, and users of contemporary analytical instruments.

SUMMARY

In accordance with the present invention, a system and method are disclosed for effectively implementing an RF power source. In one embodiment, an RF amplifier of the RF power source provides a variable-frequency RF power signal to a fixed closely-coupled impedance match that is implemented in a balanced manner. The impedance match then transfers the RF power signal to a plasma coil that is positioned adjacent to a plasma torch containing a test sample for analysis. The RF power signal is also returned through a low-pass filter to a phase-locked loop device as a reference phase signal. In addition, a phase probe is positioned near the plasma coil to sample a current operating frequency of the plasma coil. The output of the phase probe is returned through a low-pass filter to the phase-locked loop as a coil phase signal.

The phase-locked loop device then employs an RF phase comparison technique to track a peak resonance condition at the plasma coil. In practice, a phase detector of the phase-locked loop device compares the reference phase signal with the sampled coil phase signal to generate an error voltage that represents where the current operating frequency is with respect to peak resonance. A voltage-controller oscillator of the phase-locked loop device then utilizes the error voltage to generate a corresponding RF drive signal to the RF amplifier for adjusting the frequency of the RF power signal. The adjusted frequency of the RF power signal operates to drive the current operating frequency of the plasma coil in a direction towards peak resonance. At peak resonance the error voltage becomes zero volts.

Therefore, if the impedance at the plasma coil changes as a result of a varying load from the test sample in the plasma torch, an error voltage is produced with a polarity that drives the operating frequency of the plasma coil in a direction towards resonance. The loop response of the phase-locked loop is only tens of cycles of the operating frequency. The RF power source may therefore rapidly track a peak resonance condition at the plasma coil to effectively provide stable RF power and maintain a plasma state under rapid changes in load impedance. For at least the foregoing reasons, the present invention provides an improved system and method for effectively implementing an inductively-coupled plasma RF power source.

BRIEF DESCRIPTION OF THE DRAWINGS

For a better understanding of the nature and objects of the invention, reference should be made to the following detailed description, taken in conjunction with the accompanying drawings, in which.

Like reference numerals refer to corresponding parts throughout the several views of the drawings.

DETAILED DESCRIPTION OF EMBODIMENTS

The present invention relates to an improvement in analytical instrumentation techniques. The following description is presented to enable one of ordinary skill in the art to make and use the invention and is provided in the context of a patent application and its requirements. Various modifications to the disclosed embodiments will be readily apparent to those skilled in the art, and the generic principles herein may be applied to other embodiments. Thus, the present invention is not intended to be limited to the embodiments shown, but is to be accorded the widest scope consistent with the principles and features described herein.

The present invention comprises a system and method for implementing a power source, and includes a power amplifier that generates a radio-frequency power signal with an adjustable operating frequency. The power amplifier also generates a reference phase signal that is derived from the radio-frequency power signal. An impedance match provides the radio-frequency power signal to a plasma coil that has a variable resonance condition. A phase probe is positioned adjacent to the plasma coil to generate a coil phase signal corresponding to the adjustable operating frequency. A phase-locked loop then generates an RF drive signal that is based upon a phase relationship between the reference phase signal and the coil phase signal. The phase-locked loop provides the RF drive signal to the power amplifier to control the adjustable operating frequency, so that the adjustable operating frequency then tracks the variable resonance condition.

Figure 1:
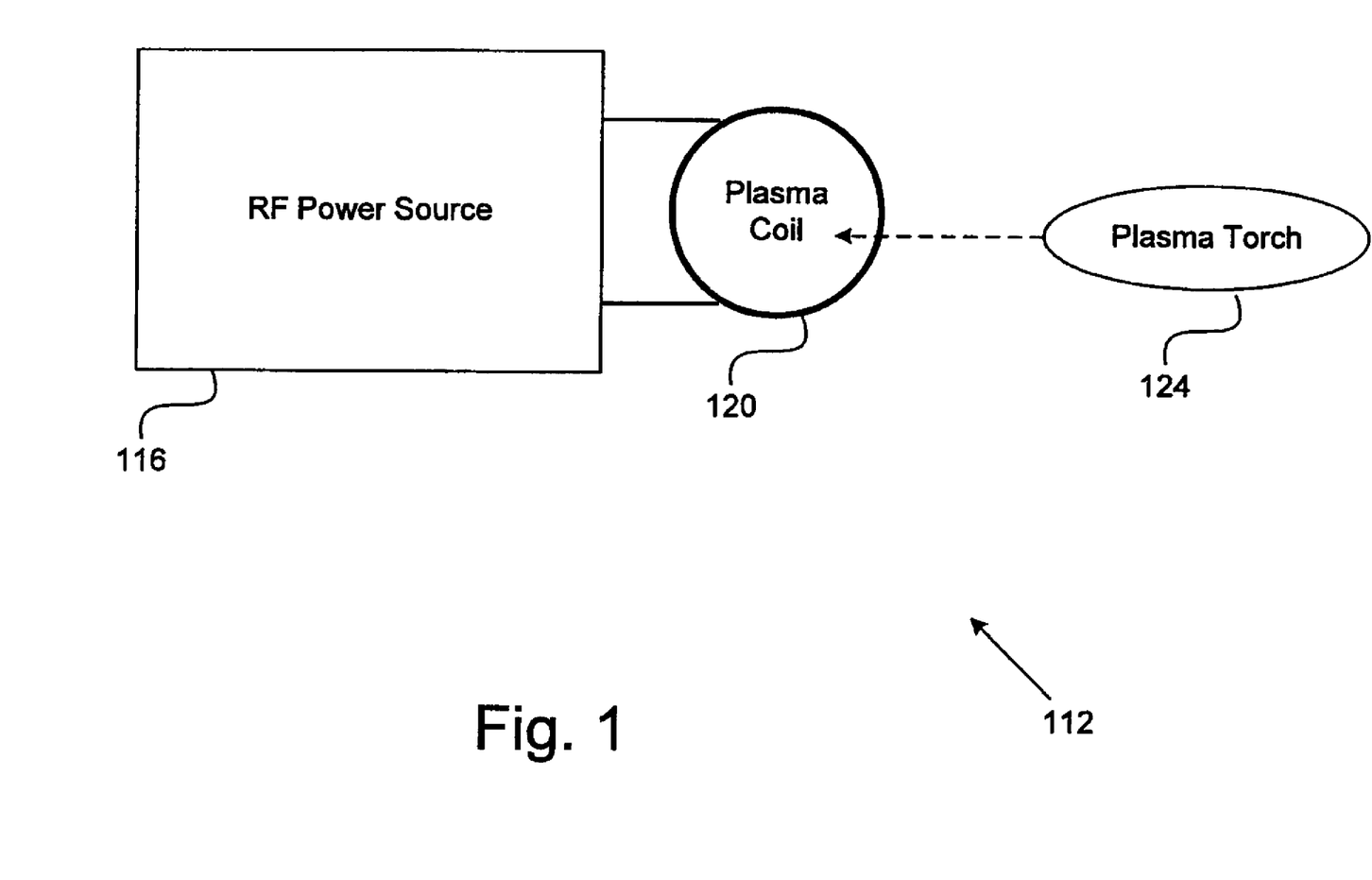
FIG. 1 is a block diagram of a plasma creation system, in accordance with one embodiment of the present invention.

Referring now to FIG. 1, a block diagram of a plasma creation system 112 is shown, in accordance with one embodiment of the present invention. In the FIG. 1 embodiment, plasma creation system 112 includes, but is not limited to, a radio-frequency (RF) power source 116, a plasma coil 120, and a plasma torch 124. In alternate embodiments, plasma creation system 112 may be implemented using components and configurations in addition to, or instead of, certain of those components and configurations discussed in conjunction with the FIG. 1 embodiment.

In the FIG. 1 embodiment, plasma creation system 112 operates to initiate and sustain a test sample in a plasma state with improved power delivery and efficiency characteristics. In the FIG. 1 embodiment, plasma creation system 112 may be utilized for any appropriate applications. For example, in certain embodiments, plasma creation system 112 may be utilized in conjunction with Inductively-Coupled Plasma Optical Emission (ICPOE) systems or with Inductively-Coupled Plasma Mass Spectrometry (ICPMS) systems.

Plasma is known as the fourth state of matter, and is composed of an ionized gas that is electrically conductive. Plasma emits electromagnetic waves that may be analyzed for identifying corresponding atomic elements in the plasma. Each element has a unique set of wavelengths, and the characteristics of a given wave set may be utilized to identify a corresponding element. A ratio of wavelength intensities may be utilized to identify the concentration of each element in a test sample that is being analyzed. The accuracy and dynamic response of the analysis measurements depend on the stability and method of delivering power to initiate and sustain the test sample in a plasma state.

In the FIG. 1 embodiment, the RF power source 116 provides RF power to a plasma coil 120. A cylindrical plasma torch 124 is typically placed adjacent to the plasma coil 120. The plasma torch 124 conducts a gas, such as argon, axially through the center of the plasma coil 120. An impedance match in RF power source 116 is employed to couple the RF power from the RF power source 116 to the plasma coil 120 to efficiently transfer RF power to the gas flowing through plasma torch 124.

Next, a high ignition voltage is discharged through a gas in plasma torch 124, and the gas releases free electrons. A test sample to be analyzed is injected into the gas stream within the plasma torch 124. The test sample is then in a conductive state to partially couple the applied RF power from the RF power source 116. A cascade process ensues to gradually increase the coupling and transfer of RF power from RF power source 116 until a full plasma state is established. During the initial ignition phase, RF power source 116 is required to supply a high level of RF power to initiate the cascade process towards a full plasma state.

As a full plasma state is being established, electrical properties of plasma coil 120 transition to a significantly different impedance. The lower impedance reduces the RF power requirement needed to sustain the plasma. The resonance frequency of plasma coil 120 varies depending on the particular test sample in plasma torch 124. In addition, the transition to a full plasma state produces significant changes in electrical properties of plasma coil 120 and plasma torch 124. RF power source 116 must therefore effectively support the dynamics of this transition. The implementation and functionality of RF power source 116 are further discussed below in conjunction with FIGS. 2 through 9.

Figure 2:
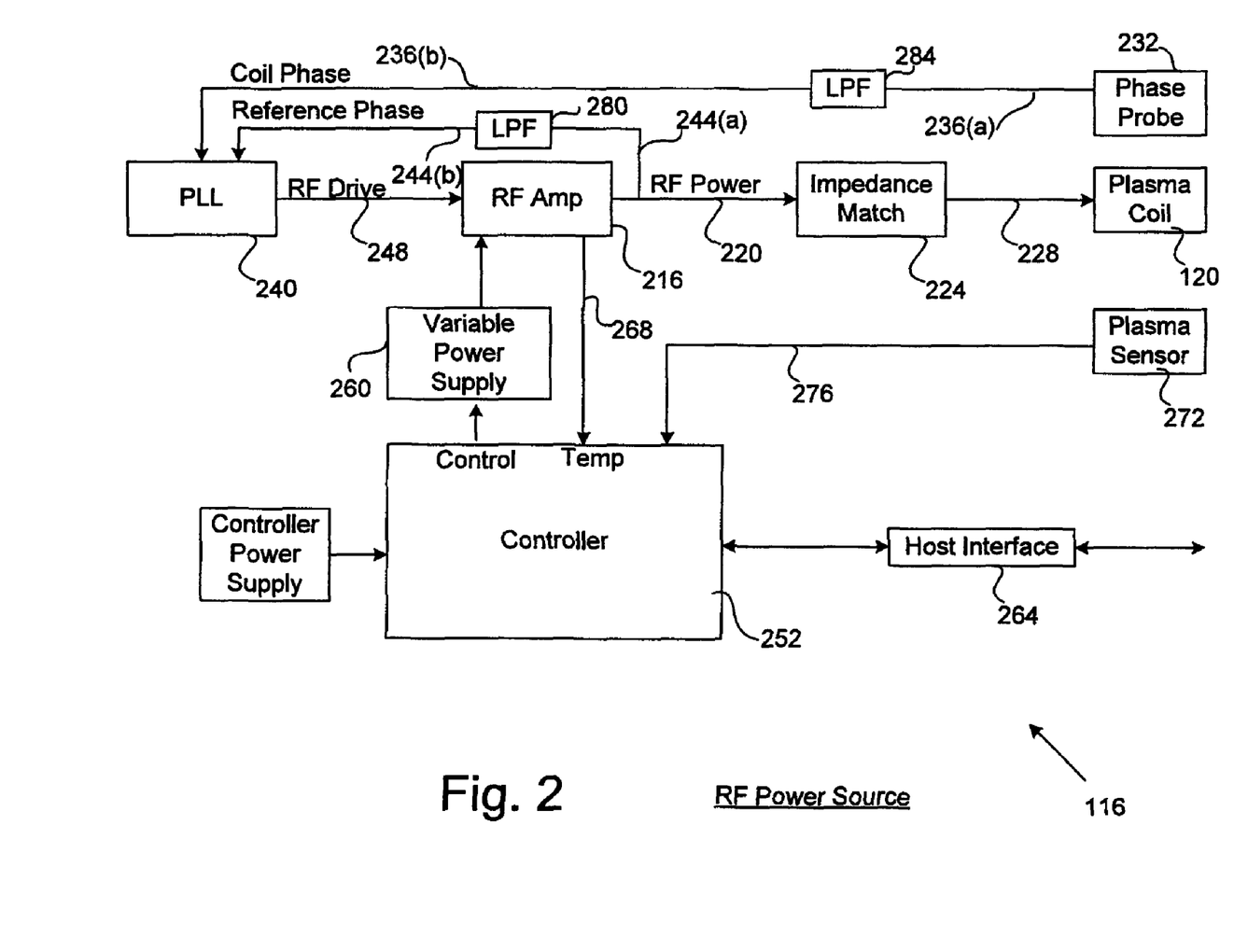
FIG. 2 is a block diagram for one embodiment of the RF power source of FIG. 1, in accordance with the present invention.

Referring now to FIG. 2, a block diagram for one embodiment of the FIG. 1 RF power source 116 is shown, in accordance with the present invention. In alternate embodiments, RF power source 116 may include components and configurations in addition to, or instead of, certain of those components and configurations discussed in conjunction with the FIG. 2 embodiment. In addition, RF power source 116 is discussed below in the context of initiating and sustaining various types of plasma. However, in certain alternate embodiments, the principles and techniques of the present invention may be applied to other appropriate contexts and applications.

In the FIG. 2 embodiment, RF power source 116 is implemented to facilitate greater power stability and an extended range of operation for plasma creation system 112 (FIG. 1). Power stability in RF power source 116 permits more accurate measurement of various different types of test samples. An extended range of operation facilitates analyzing certain test samples, such as organics, that exhibit significant impedance changes at plasma coil 120 and plasma torch 124. Increased response range to impedance changes permits testing of higher concentrations of test sample solutions.

In the FIG. 2 embodiment, an RF amplifier (RF amp) 216 provides a variable-frequency RF power signal 220 to a fixed closely-coupled impedance match 224 that then transfers the RF power signal to plasma coil 120 via path 228. The RF power signal 220 is also returned as an unfiltered reference phase signal 244($a$) through a low-pass filter (LPF) 280 to a phase-locked loop (PLL) 240 as a filtered reference phase signal 244($b$). In the FIG. 2 embodiment, LPF 280 functions to remove certain harmonic content that may be present in reference phase signal 244($a$). In addition, a phase probe 232 is positioned near plasma coil 120 to sample the current operating state of the resonant condition at plasma coil 120. In alternate embodiments, RF power source 116 may utilize any other appropriate techniques for sampling the resonant condition at plasma coil 120. For example, phase probe 232 may be located in any effective location with respect to plasma coil 120. The output of phase probe 232 is returned as an unfiltered coil phase signal 236($a$) through a low-pass filter (LPF) 284 to phase-locked loop 240 as a filtered coil phase signal 236($b$). In the FIG. 2 embodiment, LPF 284 is identical to LPF 280 and functions to provide the same time/phase shift as LPF 280 to maintain a ninety-degree phase relationship at resonance.

In the FIG. 2 embodiment, PLL 240 may then employ an RF phase comparison technique to track a peak resonance condition at plasma coil 120. In practice, PLL 240 compares filtered reference phase signal 244(b) with the filtered coil phase signal 236(b) to generate an error voltage that represents where the current operating frequency at plasma coil 120 is with respect to peak resonance. PLL 240 then utilizes the error voltage to generate a corresponding RF drive signal 248 to RF amp 216 for adjusting the frequency of RF power 220. The adjusted frequency of RF power 220 operates to drive the operating frequency of plasma coil 120 in a direction towards peak resonance. At peak resonance the error voltage becomes zero volts.

Therefore, if the impedance at plasma coil 120 changes as a result of a varying load from plasma torch 124 (FIG. 1), an error voltage is produced with a polarity that drives the operating frequency in a direction towards resonance. The loop response of PLL 240 is only tens of cycles of the operating frequency, which may nominally be set at approximately 27 MHz in certain embodiments. RF power source 116 therefore rapidly tracks a peak resonance condition at plasma coil 120 to effectively provides stable RF power and achieve a plasma state under rapid changes in load impedance.

In the FIG. 2 embodiment, a controller 252 monitors and controls certain functions of RF power source 116. For example, controller 252 may monitor various operating parameters of plasma creation system 112 (FIG. 1), such as argon pressure, coolant water flow, power loss, plasma status, plasma door interlock, maximum current, and maximum temperature. Controller 252 may receive parameter information from any appropriate source. For example, in the FIG. 2 embodiment, a plasma sensor 272 provides plasma information to controller via path 276, and one or more temperature sensors may provide temperature information to controller 252 via path 268. If any improper operating conditions are detected, controller 252 may initiate a safe shutdown procedure. If AC power is lost, controller 252 is implemented with sufficient operating power to allow controller 252 to complete the shutdown procedure. RF power source 116 may bi-directionally communicate various types of relevant information with a host system (such as a host analytical instrument) through a host interface 264.

In the FIG. 2 embodiment, a variable power supply 260 may be utilized to select a desired operating power for RF amp 216. The overall design of RF power source 116 allows for an integrated compact enclosure, where all the components, including RF amp 216, impedance match 224, controller 252, variable power supply 260, and other circuits, are housed into one modular enclosure. This stand-alone configuration enables RF power source 116 to be incorporated into various analytical instruments without modification. All the components of the RF power source 116 are housed in a common enclosure to make shielding radio-frequency emissions more effective. The implementation and utilization of RF power source 116 is further discussed below in conjunction with FIGS. 3-9.

Figure 3:
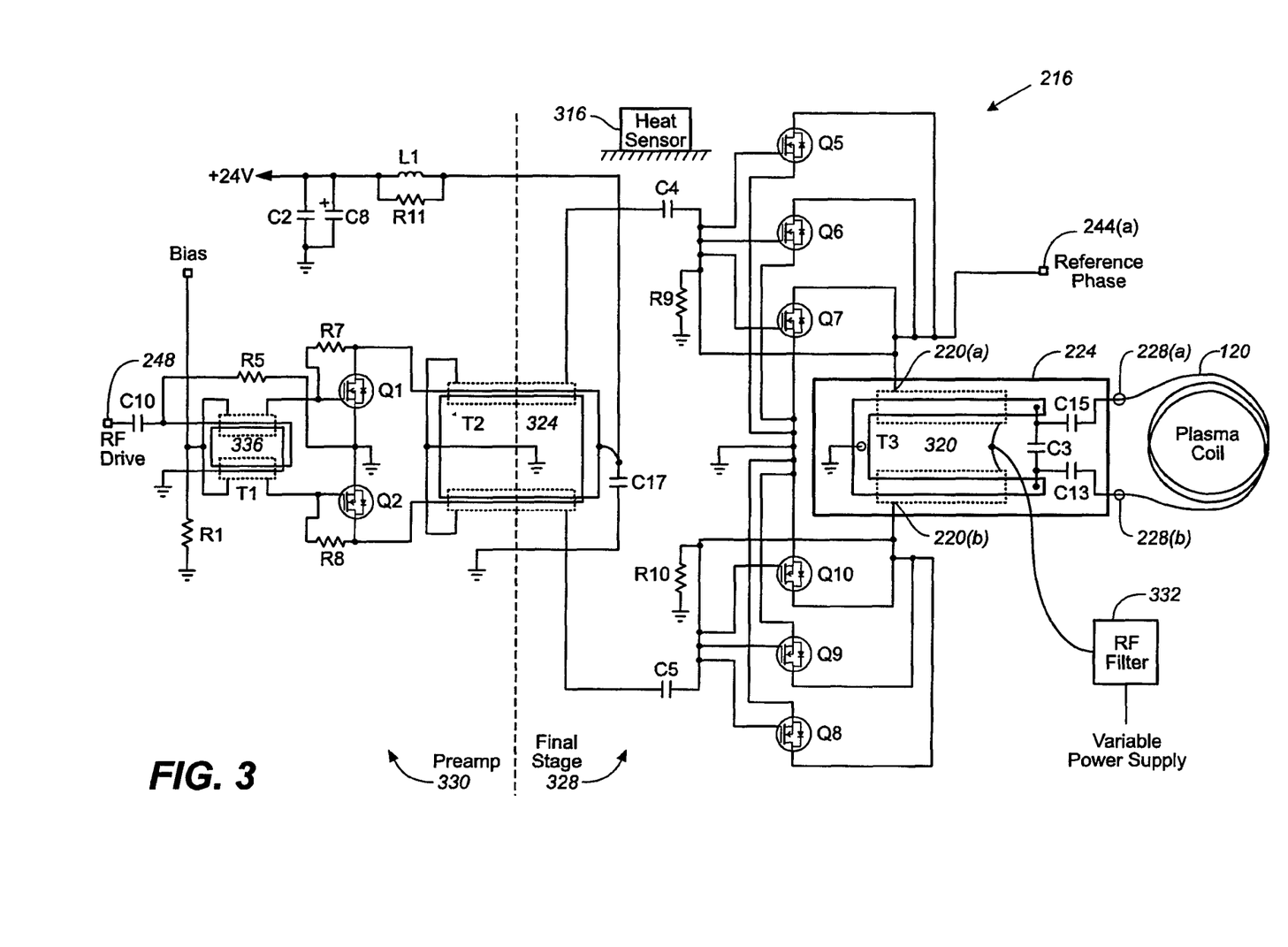
FIG. 3 is a schematic diagram for one embodiment of the impedance match and RF amp of FIG. 2, in accordance with the present invention.

Referring now to FIG. 3, a schematic diagram for one embodiment of the FIG. 2 RF amp 216 and the FIG. 2 impedance match 224 is shown, in accordance with the present invention. In alternate embodiments, RF amp 216 and impedance match 224 may include components and configurations in addition to, or instead of, certain of those components and configurations discussed in conjunction with the FIG. 3 embodiment.

In the FIG. 3 embodiment, a preamplifier stage (preamp) 330 of RF amp 216 receives an RF drive signal 248 from PLL 240 (FIG. 2) at a given adjustable frequency that is determined by PLL 240. Preamp 330 then passes the RF drive signal 248 through transformer 1 (T1) 336, transistors Q1 and Q2, and transformer 2 (T2) 324 to final stage 328 of RF amp 216. A first transistor bank of transistors Q5, Q6, and Q7, and a second transistor bank of transistors Q8, Q9, and Q10 are arranged in a push-pull amplifier configuration to receive the RF signal from T2 324, and generate a balanced RF power signal to impedance match 224 through connections 220(a) and 220(b). Impedance match 224 then passes the RF Power signal to plasma coil 120 through connections 228(a) and 228(b). In addition, the RF power output signal of RF amp 216 is sampled at connection 220(a), and is provided in a feedback loop to PLL 240 (FIG. 2) as a reference phase signal 244(a).

In the FIG. 3 embodiment, RF amp 216 has a power amplifier bias to operate in a class E mode for improved efficiency by completely saturating Q5, Q6, Q7, Q8, Q9, and Q10. The power amplifier may also be configured to operate with Q5, Q6, Q7, Q8, Q9 in a more linear or unsaturated class B mode of operation for reduced efficiency so as to sustain a plasma with a power level lower than can be achieved in the saturated mode. This mode is advantageous for certain applications of mass spectrometry. The design of RF amp 216 exhibits a wide bandwidth with a flat response that delivers constant power over the range of operating frequencies of RF power source 116 (FIG. 2). Power amp 216 is directly close-coupled to impedance match 224, thus eliminating the need for a coaxial feed cable. Close coupling permits operating at impedances other than the characteristic impedance of a system that utilizes a 50 Ohm coaxial cable. Power amp 216 may therefore operate with dynamic impedance to allow for a greater range of operating impedances at plasma coil 120 and plasma torch 124. Close coupling also avoids limited dynamic range and radiation of unwanted RF often associated with coaxial cables.

Impedance match 224 is fixed (without variable components) to eliminate the need for variable capacitors and servo systems, which are often slow, cumbersome, and costly. The delivery of RF power from RF amp 216 through impedance match 224 to plasma coil 120 utilizes a balanced configuration with a grounded center tap. In alternate embodiments, an unbalanced configuration may be utilized. In the FIG. 3 embodiment, T3 320 is implemented as an RF ferrite transformer that operates at an impedance of 5 Ohms or less, depending on RF power requirements. In an alternate embodiment, the transformer T3 may be replaced by a center-tapped inductor L2. This functions to de-couple the RF component from the variable power supply. The load presented to the power amplifier at 220(a) and 220(b) is 5 ohms or less, depending on RF power requirements. The RF power signal from RF amp 216 at connections 220(a) and 220(b) is configured to provide a balanced RF power signal into impedance match 224. Similarly, impedance match 224 is configured to drive plasma coil 120 in a balanced manner at connections 228(a) and 228(b). The result is an RF field that is balanced around a ground potential. Therefore, the highest voltage required in RF power source 116 is reduced by one half.

Variations in the operating conditions of RF amp 216 and impedance match 224 may produce unwanted resonance shifts that result in power delivery variations. To maintain stable operating conditions, impedance match 224 is held at a constant temperature using a water cooling means. In certain embodiments, impedance match 224 is therefore maintained at a constant temperature to reduce changes in component values. In addition, RF power source 116 includes a heat sensor 316 that provides temperature information to controller 252 of FIG. 2. In the FIG. 3 embodiment, a variable power supply 260 (FIG. 2) provides center-tapped operating power to impedance match 224 for powering final stage 328 of RF amp 216. In the FIG. 3 embodiment, an RF filter 332 prevents unwanted radio-frequencies from leaking into the variable power supply 260. The utilization of RF power amp 216 and impedance match 224 is further discussed below in conjunction with FIGS. 7-9.

Figure 4:
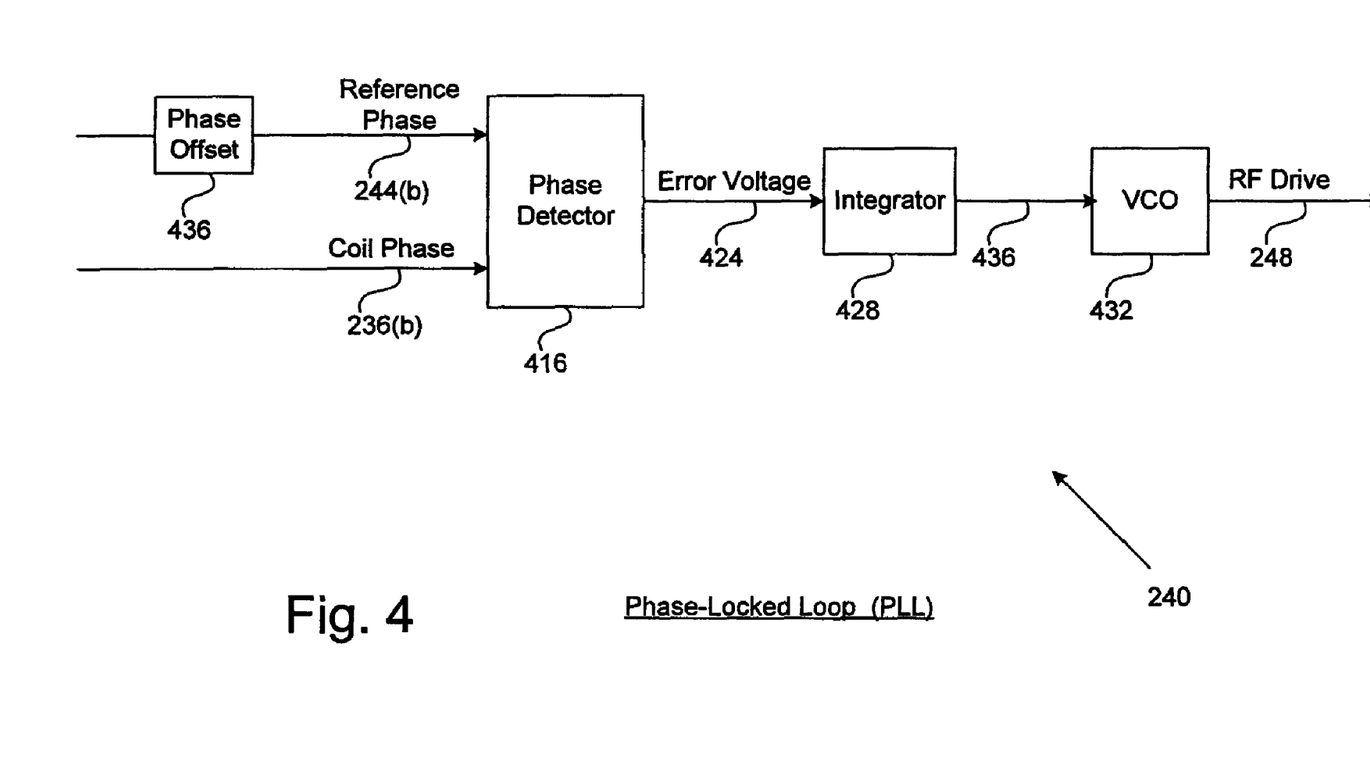
FIG. 4 is a block diagram for one embodiment of the phase-locked loop of FIG. 2, in accordance with the present invention.

Referring now to FIG. 4, a block diagram for one embodiment of the FIG. 2 phase-locked loop (PLL) 240 is shown, in accordance with the present invention. In the FIG. 4 embodiment, PLL 240 includes, but is not limited to, a phase detector 416, an integrator 428, and a voltage-controller oscillator (VCO) 432. In alternate embodiments, PLL 240 may include components and configurations in addition to, or instead of, certain of those components and configurations discussed in conjunction with the FIG. 4 embodiment.

In order for RF power source 116 (FIG. 1) to deliver full RF power to plasma torch 124 (FIG. 1), the operating frequency of the RF power 220 (FIG. 2) should preferably correspond with the natural peak resonance frequency of impedance match 224 (FIG. 3). In the FIG. 4 embodiment, a phase-lock control feedback loop with phase detector 416 and voltage-controlled oscillator (VCO) 432 is utilized to control the phase relationship (and hence the frequency) between reference phase signal 244(*b*) derived from the output of RF amp 216 (FIG. 2) and coil phase signal 236(*b*) derived from the output of phase probe 232 (FIG. 2).

To track a peak resonance condition at plasma coil 120, phase detector 416 must produce a zero error voltage 424. Because of certain operational characteristics of phase detector 416, the reference phase signal 244(*b*) and the coil phase signal 236(*b*) must be 90 degrees out-of-phase with respect to each other in order to generate a zero error voltage 424. If the phase relationship should differ from ninety degrees, then the error voltage 424 from phase detector 416 would be either positive or negative, depending on whether the phase difference was greater or less than 90 degrees. In the FIG. 4 embodiment, reference phase signal 244(*b*) is derived from the RF power signal 220 that is output from RF amp 216, and coil phase signal 236(*b*) is derived from the output of phase probe 232, because there exists an inherent 90 degree phase shift relationship between reference phase signal 244(*b*) and coil phase signal 236(*b*) as derived from those locations.

In the FIG. 4 embodiment, error voltage 424 is provided to an integrator 428 that amplifies error voltage 424 and removes any unwanted radio-frequency components in error voltage 424. Integrator 428 then provides the integrated error voltage 424 to VCO 432 via path 436. VCO 432 responsively generates an RF drive signal 248 that has a RF drive frequency which is determined by the amplitude and polarity of the error signal 424 received from integrator 428. PLL 240 then provides the RF drive signal 248 to RF amp 216 (FIG. 2) to adjust the operating frequency of the RF power signal 220 that is provided to impedance match 224 (FIG. 3). In the FIG. 4 embodiment, PLL 240 may be implemented to include a phase offset 436 that causes phase detector 416 to responsively adjust the frequency of RF drive signal 248 so that plasma coil 120 operates on the slope of resonance, rather than at peak resonance. For example, in certain embodiments, phase offset 436 may be implemented by altering the length of the path of reference phase 244(*b*). One example for operating on the slope of resonance is discussed below in conjunction with FIG. 6. The utilization of PLL 240 is further discussed below in conjunction with FIGS. 5-9.

Figure 5:
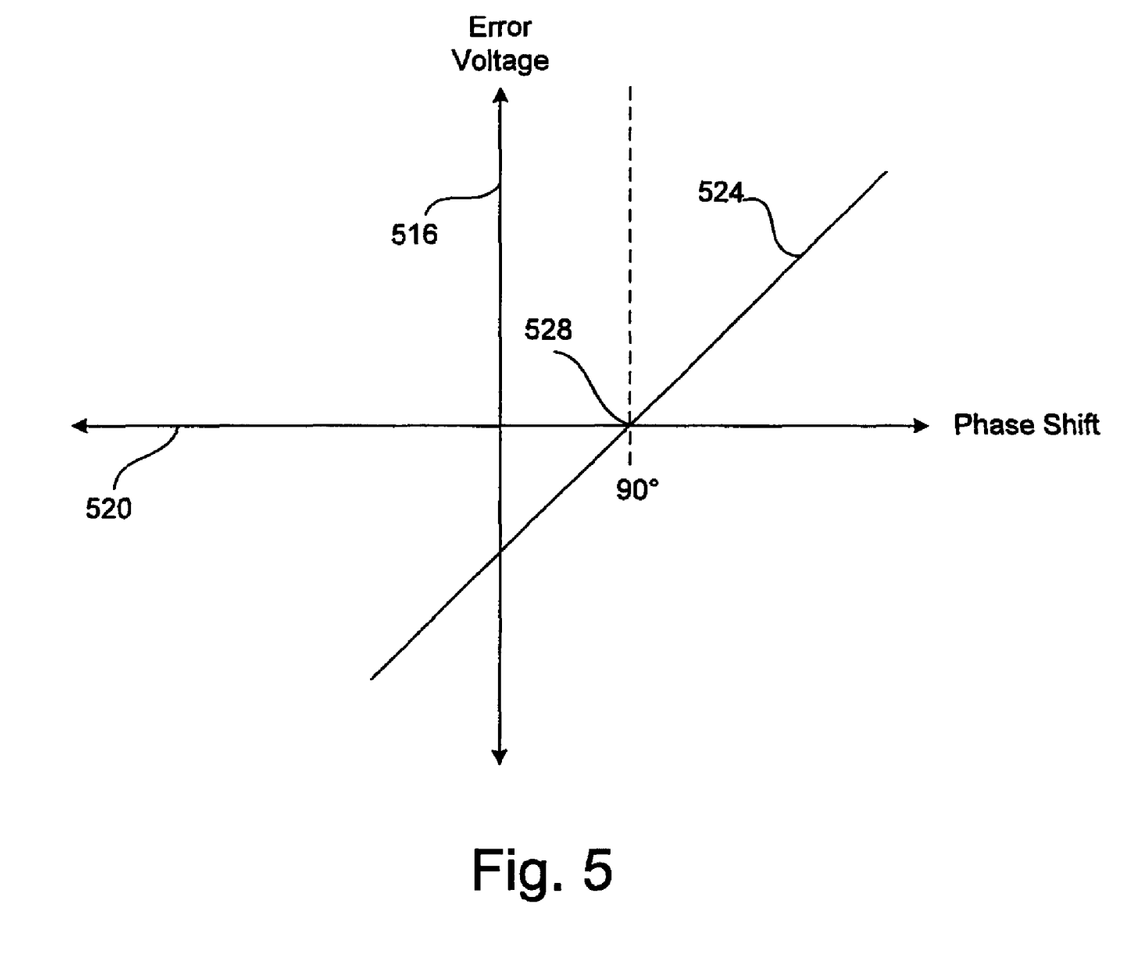
FIG. 5 is a graph illustrating a phase shift-error voltage relationship, in accordance with one embodiment of the present invention.

Referring now to FIG. 5, a graph illustrating a phase shift-error voltage relationship is shown, in accordance with one embodiment of the present invention. The FIG. 5 graph is presented for purposes of illustration, and in alternate embodiments, the present invention may utilize phase shift-error voltage relationships with properties and characteristics in addition to, or instead of, certain of those properties and characteristics discussed in conjunction with the FIG. 5 embodiment.

In the FIG. 5 embodiment, phase shift values between reference phase signals 244 and coil phase values 236 (FIG. 2) are shown on a horizontal axis 520. In addition, error voltages 424 (FIG. 4) from phase detector 416 of PLL 240 are shown on a vertical axis 516. A line 524 is plotted to represent exemplary phase-shift-error voltage relationships. For purposes of illustration, the FIG. 5 phase-shift-error voltage relationship is shown as being linear. However, in alternate embodiments, various types of non-linear relationships are equally contemplated. As discussed above in conjunction with FIG. 4, at a phase shift of ninety degrees, a peak resonance condition 528 is shown on the FIG. 5 graph with an error voltage of zero volts. In the FIG. 5 example, as the phase shift increases above ninety degrees, the error voltage increases, and as the phase shift decreases below ninety degrees, the error voltage decreases.

Figure 6:
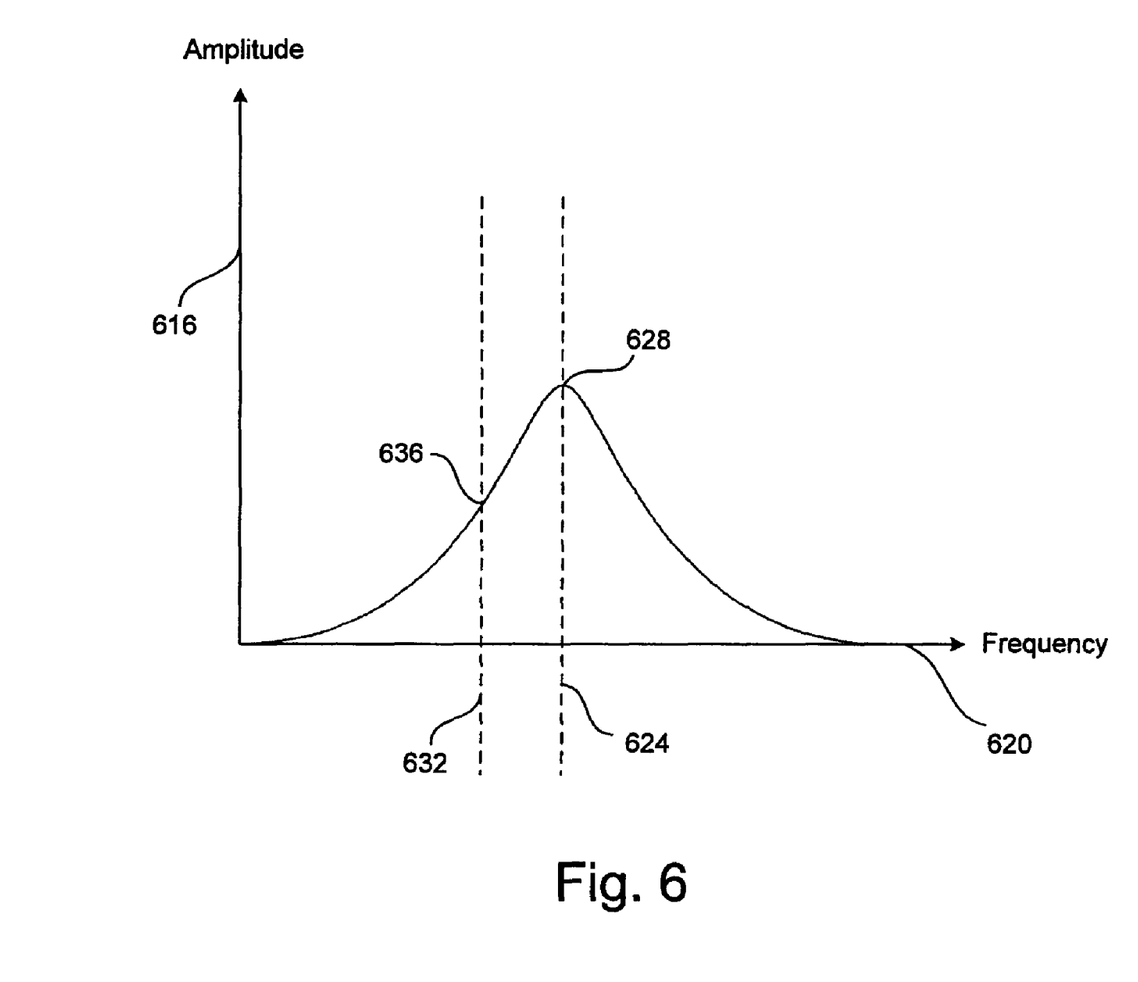
FIG. 6 is a graph illustrating a technique for operating on a resonance slope, in accordance with one embodiment of the present invention.

Referring now to FIG. 6, a graph illustrating a technique for operating on a resonance slope is shown, in accordance with one embodiment of the present invention. The FIG. 6 graph is presented for purposes of illustration, and in alternate embodiments, the present invention may operating on a resonance slope using values and techniques in addition to, or instead of, certain of those values and techniques discussed in conjunction with the FIG. 6 embodiment.

In the FIG. 6 embodiment, operating frequency values for plasma coil 120 (FIG. 2) are shown on a horizontal axis 620. In addition, amplitudes of RF operating power at plasma coil 120 are shown on a vertical axis 616. A bell-shaped curve is plotted to represent values from exemplary resonance conditions at plasma coil 120. In the FIG. 6 embodiment, a peak resonance condition 628 is shown at peak resonance frequency 624. RF power source 116 may be operated on the slope of resonance so that the operating frequency of plasma coil 120 is selectively chosen at a location that is not directly at peak resonance 628. In the FIG. 6 embodiment, RF power source 116 is being operated at slope point 636 at frequency 632. Operating RF power source 116 on the slope of resonance may be desirable under various types of analysis conditions, and may provide the ability to tailor response characteristics of RF power source 116 for improved performance in certain operating environments.

Figure 7:
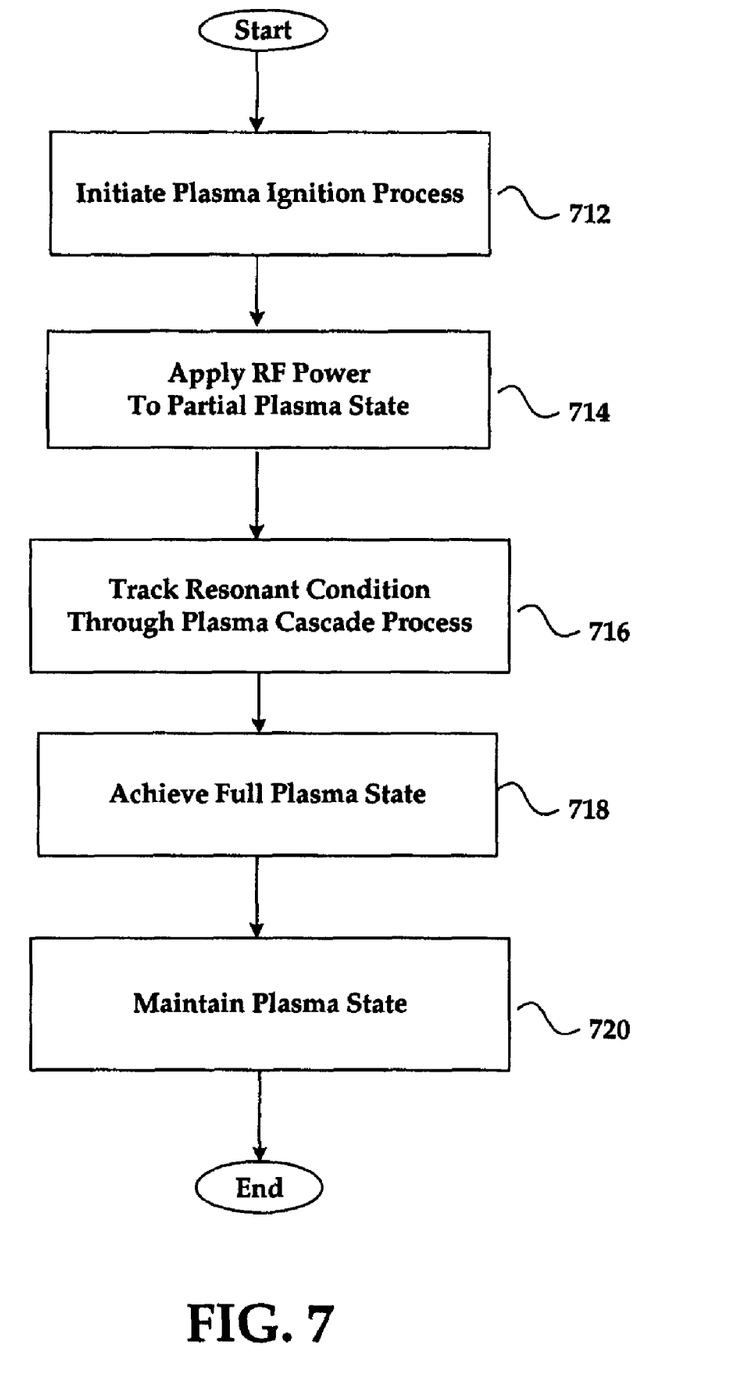
FIG. 7 is a flowchart of method steps for tracking a resonant condition during a plasma creation process, in accordance with one embodiment of the present invention.

Referring now to FIG. 7, a flowchart of method steps for tracking a resonant condition during a plasma creation process is shown, in accordance with one embodiment of the present invention. The FIG. 7 example is presented for purposes of illustration, and in alternate embodiments, the present invention may utilize steps and sequences other than certain of those steps and sequences discussed in conjunction with the FIG. 7 embodiment.

In the FIG. 7 embodiment, in step 712, RF power source 116 (FIG. 2) initiates a plasma creation process by utilizing any appropriate techniques. For example, in certain embodiments, RF power source 116 may initially provide a high-voltage ignition charge to a gas in plasma torch 124 (FIG. 1). In step 714, RF power source 116 applies an RF power signal 220 from plasma coil 120 to a test sample in a partial plasma state in plasma torch 124. In step 716, RF power source 116 tracks a resonant condition at plasma coil 120 through a changing plasma cascade process by adjusting the current operating frequency of the RF power signal 220 provided to plasma coil 120. In step 718, the test sample in plasma torch 124 achieves a full plasma state. Finally, in step 720, RF power source 116 maintains the full plasma state achieved in foregoing step 718 to facilitate various analysis procedures for the test sample.

Figure 8:
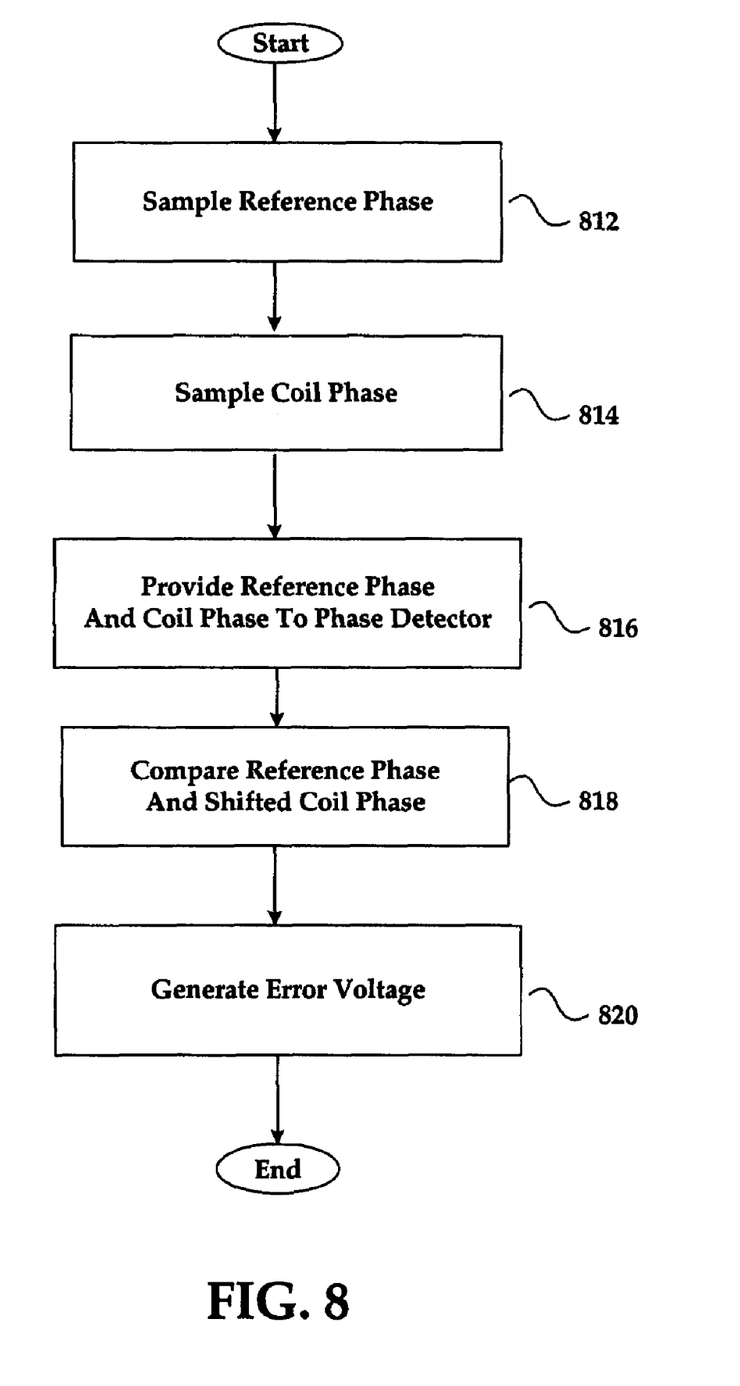
FIG. 8 is a flowchart of method steps for generating an error voltage, in accordance with one embodiment of the present invention.

Referring now to FIG. 8, a flowchart of method steps for generating an error voltage 424 (FIG. 4) is shown, in accordance with one embodiment of the present invention. The FIG. 8 example is presented for purposes of illustration, and, in alternate embodiments, the present invention may utilize steps and sequences other than certain of those steps and sequences discussed in conjunction with the FIG. 8 embodiment.

In the FIG. 8 embodiment, in step 812, RF power source 116 initially samples a reference phase signal 244 for generating an error voltage 424. In certain embodiments, reference phase signal 244 may be derived from an RF power signal 220 from RF amp 216 (FIG. 2). Then, in step 814, RF power source 116 samples a coil phase signal 236 that is generated by a phase probe 232 adjacent to plasma coil 120 (FIG. 2). In step 816, RF power source 116 provides the reference phase signal 244 and the coil phase signal 236 to a phase detector 416 of a phase-locked loop 240 (FIG. 2). Next, in step 818, phase detector 416 compares the reference phase signal 244 and the coil phase signal 236 by utilizing any appropriate means. Finally, in step 820, phase detector 416 generates error voltage 424 to represent the direction and the magnitude of phase shift between reference phase signal 244 and coil phase signal 236.

Figure 9:
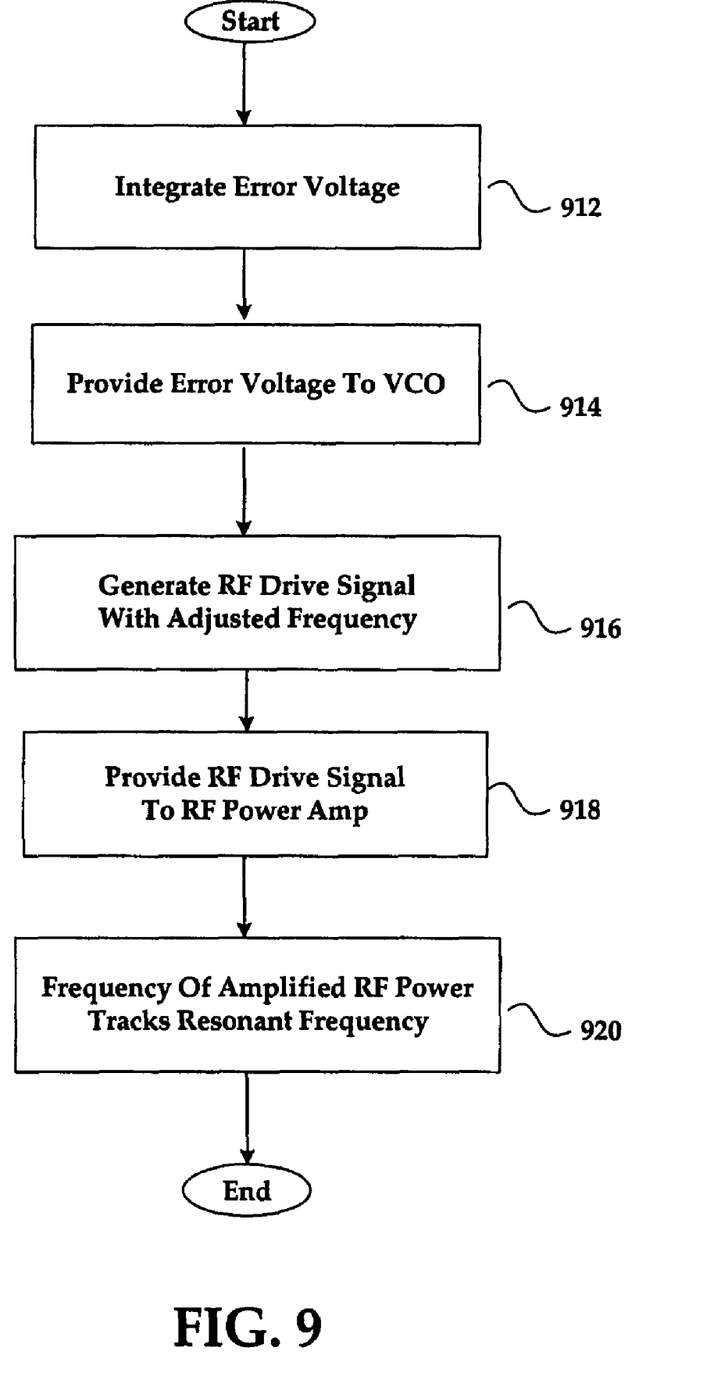
FIG. 9 is a flowchart of method steps for adjusting an RF operating frequency, in accordance with one embodiment of the present invention.

Referring now to FIG. 9, a flowchart of method steps for adjusting an RF operating frequency is shown, in accordance with one embodiment of the present invention. The FIG. 9 example is presented for purposes of illustration, and, in alternate embodiments, the present invention may utilize steps and sequences other than certain of those steps and sequences discussed in conjunction with the FIG. 9 embodiment.

In the FIG. 9 embodiment, in step 912, integrator 428 of PLL 240 (FIG. 4) integrates the error voltage 424, generated by phase detector 416 (FIG. 4) during step 820 of FIG. 8, to remove certain unwanted radio-frequency components. Then, in step 914, integrator 428 provides the integrated error voltage to a voltage-controlled oscillator (VCO) 432 of PLL 240. In step 916, VCO 432 generates an RF drive signal that has a drive frequency which corresponds to the amplitude and polarity of error voltage 424. In step 918, PLL 240 provides the RF drive signal 248 to the RF power amp 216 of RF power source 116.

Finally, in step 920, in response to the drive frequency of RF drive signal 248, RF power amp 216 generates RF power signal 220 with a frequency that tracks the current peak resonant frequency of plasma coil 120. The foregoing FIG. 8 error voltage generation procedure and FIG. 9 RF operating-frequency adjustment procedure are typically repeated on an ongoing basis to allow RF power source 116 to track and maintain operating parameters at current resonant conditions. For at least the foregoing reasons, the present invention provides an improved system and method for implementing an inductively-coupled RF power source.

The invention has been explained above with reference to certain embodiments. Other embodiments will be apparent to those skilled in the art in light of this disclosure. For example, the present invention may be implemented using configurations and techniques other than certain of those configurations and techniques described in the embodiments above. Additionally, the present invention may effectively be used in conjunction with systems other than those described above. Therefore, these and other variations upon the discussed embodiments are intended to be covered by the present invention, which is limited only by the appended claims.

What is claimed is:

1. A system for implementing a power source, comprising:
a power amplifier that generates a radio-frequency power signal with an adjustable operating frequency;
an impedance match that provides said radio-frequency power signal to a plasma coil that has a variable resonance condition;
a phase-locked loop device that generates a drive signal to said power amplifier to control said adjustable operating frequency;
a first power control loop including a variable power supply for supplying power to the power amplifier and a power supply controller for monitoring the power supplied to the power amplifier and controlling the variable power supply in response thereto to supply a desired power to the power amplifier; and
a second control loop including a phase probe positioned adjacent to said plasma coil to generate a coil phase signal corresponding to said adjustable operating frequency;
wherein the power amplifier also generates a reference phase signal derived from said radio-frequency power signal; and
wherein the drive signal generated by the phase-locked loop device is based upon a phase relationship between said reference phase signal and said coil phase signal, said adjustable operating frequency then tracking said variable resonance condition to provide substantially stable power transfer from the power amplifier to the plasma coil.

2. The system of claim 1 wherein a phase detector of said phase-locked loop device receives and compares said reference phase signal and said coil phase signal to determine said phase relationship.

3. The system of claim 2 wherein said phase detector generates an error voltage that represents a magnitude and a polarity of said phase relationship.

4. The system of claim 3 wherein said error voltage is equal to zero volts if said adjustable operating frequency is equal to said variable resonance condition.

5. The system of claim 4 wherein said reference phase signal and said coil phase signal are sampled so that said phase relationship is ninety degrees out-of-phase when said error voltage is equal to zero volts.

6. The system of claim 3 wherein said phase detector adjusts said error voltage so that said adjustable operating frequency is set to a resonance slope frequency that is different from a peak resonance frequency of said plasma coil.

7. The system of claim 3 wherein an integrator device performs a filtering process upon said error voltage to remove unwanted radio-frequency components.

8. The system of claim 3 wherein a voltage-controller oscillator of said phase-locked loop device generates said drive signal at said adjustable operating frequency in response to an amplitude and a polarity of said error voltage.

9. The system of claim 1 wherein said power amplifier is operated in a Class E mode to limit power consumption requirements.

10. The system of claim 1 wherein said power amplifier of said power source is directly close-coupled to said impedance match.

11. The system of claim 1 wherein said impedance match has dynamic variable impedance characteristics with respect to said power amplifier.

12. The system of claim 1 wherein said impedance match is implemented with fixed non-adjustable electronic components.

13. The system of claim 1 wherein said impedance match transfers said radio-frequency power signal from said power amplifier to said plasma coil in a balanced manner, said impedance match including a radio-frequency transformer with a grounded center tap.

14. The system of claim 1 wherein said impedance match transfers said radio-frequency power signal from said power amplifier to said plasma coil in an unbalanced manner, said impedance match including a radio-frequency transformer with an ungrounded center tap.

15. The system of claim 1 wherein said plasma coil of said power source is utilized to initiate and sustain a test sample in a plasma state within a plasma torch for analysis with at least one of an optical emission measurement technique and a mass spectrometry measurement technique.

16. The system of claim 1 further comprising a controller device of said power source, said controller device monitoring a plasma status of a test sample being analyzed, said controller device also monitoring a temperature parameter from a heat sensor in said power source.

17. The system of claim 1 wherein said impedance match is implemented with temperature stabilization provided by an adjacent cooling mechanism.

18. The system of claim 1 wherein said power source includes a host interface to permit bi-directional communications between said power source and an external host device.

19. The system of claim 1 wherein said power source is implemented as a self-contained modular device to facilitate incorporating said power source into a host analytical instrument without modifications.

20. The system of claim 1 wherein said power amplifier is operated in a class B mode to reduce an efficiency of power generation for sustaining a low-power plasma operation.

21. A method for implementing a power source, comprising:
generating a radio-frequency power signal with an adjustable operating frequency by utilizing a power amplifier;
utilizing an impedance match to provide said radio-frequency power signal to a plasma coil that has a variable resonance condition; and
generating a drive signal to said power amplifier from a phase-locked loop device to control said adjustable operating frequency;
operating a first power control loop, by:
supplying power to the power amplifier from a variable power supply; and
using a power supply controller to monitor the power supplied to the power amplifier and control the variable power supply in response thereto to supply a desired power to the power amplifier; and
operating a second control loop, by:
generating a reference phase signal derived from said radio-frequency power signal from the power amplifier;
positioning a phase probe adjacent to said plasma coil to generate a coil phase signal corresponding to said adjustable operating frequency; and
generating the drive signal to said power amplifier based upon a phase relationship between said reference phase signal and said coil phase signal, said adjustable operating frequency then tracking said variable resonance condition to provide substantially stable power transfer from the power amplifier to the plasma coil.

* * * * *